United States Patent [19]

Brownlee

[11] 4,347,131

[45] Aug. 31, 1982

[54] LIQUID CHROMATOGRAPHIC PUMP MODULE

[76] Inventor: Robert Brownlee, 26050 Kriste La., Los Altos Hills, Calif. 94022

[21] Appl. No.: 258,404

[22] Filed: Apr. 28, 1981

[51] Int. Cl.³ ............................................. B01D 15/08
[52] U.S. Cl. ................................. 210/101; 210/198.2
[58] Field of Search ............................. 210/101, 198.2

[56] References Cited

U.S. PATENT DOCUMENTS 4,191,649 3/1980 Hartwick ........................ 210/198.2
4,233,156 11/1980 Tsukada ........................ 210/198.2
4,310,420 1/1982 Konishi ........................ 210/101 X Primary Examiner—John Adee
Attorney, Agent, or Firm—Robert B. Block

[57] ABSTRACT

Pump module for liquid chromatography for delivering the mobile phase to a separation column under high pressure including a cylinder containing a plunger and forming a syringe pump, a seal disposed between the plunger and cylinder, two positive action valves connect to the output of the pump either to a reservoir of said mobile phase or to a sample injection valve. The pump is dimensioned to accommodate most chromatographic analysis i.e. from about 10 ml to 40 ml.

8 Claims, 4 Drawing Figures

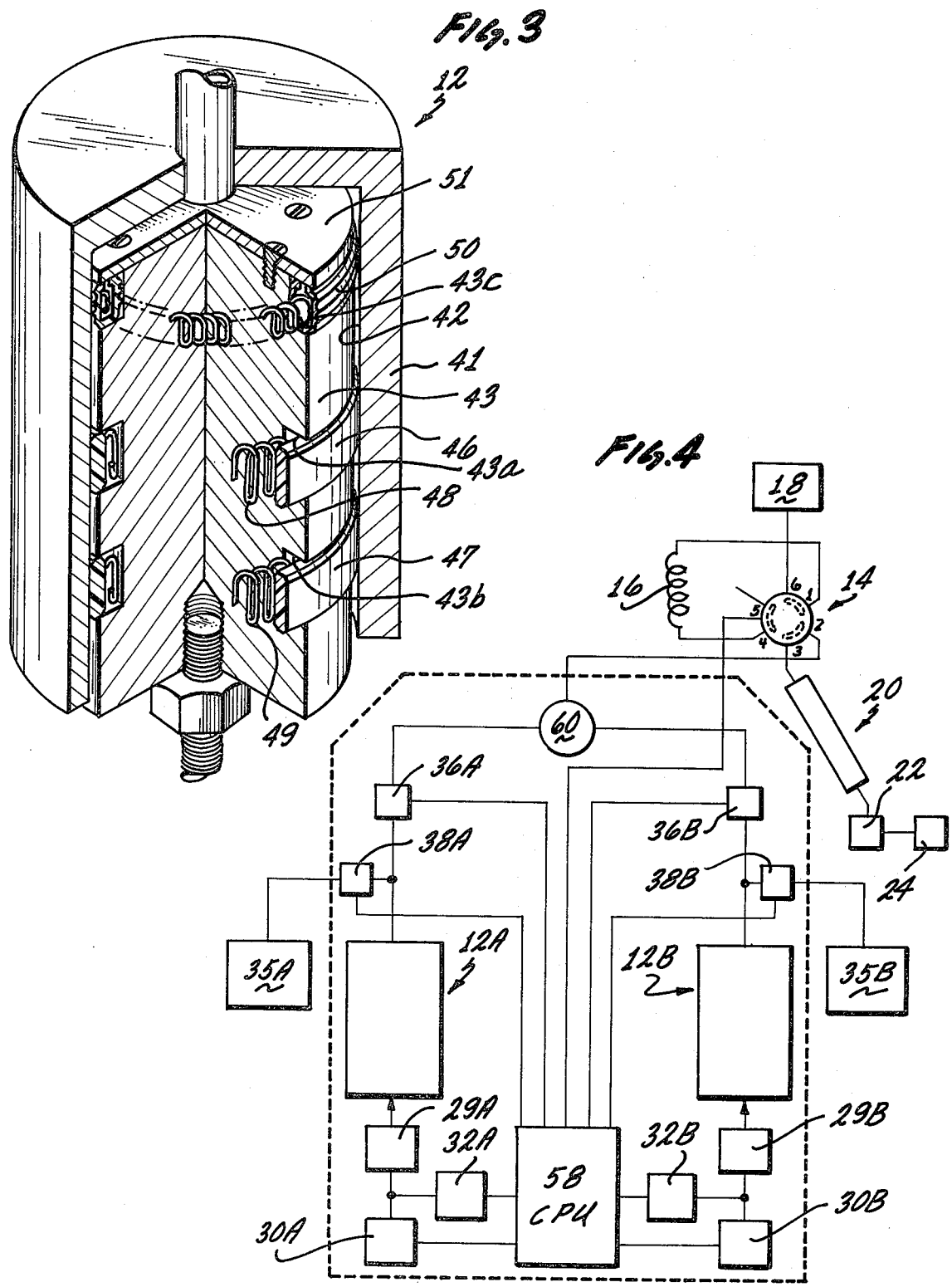

LIQUID CHROMATOGRAPHIC PUMP MODULE

TECHNICAL FIELD

This invention relates to liquid chromatography, and more particularly to a liquid chromatographic pump module suitable for use in the majority of routine liquid chromatographic analysis procedures under either isocratic or gradient elution conditions. The abbreviation LC will be used throughout the present application to indicate liquid chromatographic systems in general and their component parts.

BACKGROUND OF INVENTION

Heretofore, pumping systems for LC analysis equipment has been generally characterized by the use of a pump for delivering a mobile phase liquid to a separation column under elevated pressure. Injection means is interposed between the pump and the separation column for adding a liquid sample to be carried through the column by the mobile phase.

Generally, LC equipment has been designated to render the maximum possible performance over a wide variety of conditions. Typically LC equipment is designed for operating pressures above 3,000 psi and often is specified for operation from 5,000 to 10,000 psi. Equipment as specified for use at these pressures are indeed capable of nearly all LC analysis which may be required. Many pumping designs have been utilized in the past, among these include the use of syringe pumps of the order of 500 to 1,000 milliliter capacity, have been as available from Varian Aerograph of Walnut Creek, Calif.; Perkin Elmer, Inc. of Norwalk, Conn. and Isco (Instrument Specialty Company) of Nebraska.

In such liquid chromatographic applications the most common form of syringe pump has been of the size of 500 ml or higher and designed for operation at a designated pressure of 8,500 psi. Syringe pumps of this size were amongst the earlier pumps used in LC. The early success of the syringe pump relied on its mechanical simplicity and reliability and the fact that it is a positive displacement system producing very accurate flow rate deliveries. However, it came into criticism on theoretical and practical grounds because the high pressures and large volumes of these pumps were shown to be detrimental to performance. It can be shown that for a 1,000 ml volume syringe pump filled with hexane, a common hydrocarbon liquid solvent used in LC, the volume of the hexane would be compressed by an appreciable percentage greater than 1% at such pressures. Therefore, in a closed-off operation with no flow, the pump may have to move a considerable distance over an equally considerable time before normal operating pressure is achieved because the first part of the action would be taken up doing work in compressing the hexane. In dynamic situations this means that, after the pump is turned on, it could take up to twenty minutes before accurate flow rate was achieved. Further, the large size of the parts involved a certain mechanical compliance of the system which is directly proportional to scale. As an example, for 1 ml flow per minute, such pumps are operated using only one part per thousand of its total volume per minute. Thus, imperfections in the mechanical system, or its tolerances, or the compressibility errors due to operation over such a small percentage of the total capacity of the pump result in such errors being magnified. In the past it was common to manually fill such syringe pumps. This in itself was sufficiently inconvenient so as to induce manufacturers to use a large volume pump so as to reduce the refill cycle time. Thus, there is a need for a lower flow rate pump which has a better compositional accuracy of the delivered flow and which is not subject to compressibility factors and compliance factors to the degree of prior art large volume syringe pumps. In one known system an exceedingly small syringe pump having a volume of about 1 ml has been available for operation at pressures of approximately 2,000 psi.

Most other commercial LC pumps are small syringe pumps (about 0.020 to 0.10 ml) which are driven cyclically at 0.0 to 300 Hertz with a separate inlet check valve and outlet check valve, both of which are usually passively actuated. Such pump cannot produce the very low flow rates at low or moderate pressure needed for LC due to valve leakage and high flow rate design. Because these pumps are refilled and emptied many times during the course of a single LC analysis, they cause noise and spurious responses in detector output signal.

There is therefore a need for a new pumping system for liquid chromatographs which will overcome the foregoing disadvantages and limitations.

OBJECTS OF THE INVENTION

In general it is an object of the present invention to provide a pumping system for liquid chromatographs which in the majority of cases will perform better than prior pumping systems and at a lower cost.

A further object of the invention is to provide a liquid chromatographic pumping system of the above character in which the characteristics of the pump are closely coupled to the needs of a real time analytical system particularly for high accuracy, low flow rate, and better compositional accuracy of the delivered flow.

It is a further object of the invention to provide a liquid chromatographic pumping system of the above character which is especially designed to optimize its performance in the majority of applications of liquid chromatographic systems.

SUMMARY OF THE INVENTION

The present invention is predicated on the realization that syringe pumps as known in the past have been of too large of volume and that it is possible to provide a pump of relatively low volume as for example about 40 ml which will operate satisfactorily as a single shot, batch pumping system. Active valving is connected to such a pump and coordinated with its flow by a refill controller to provide optimum performance over the wide range of LC operations. More specifically, the liquid chromatographic apparatus of the present invention includes a separation column having a stationary phase through which the pump drives a mobile phase carrying a sample having components to be separated by differential adsorption. The pump is a one shot delivery system and includes means for refilling the same including a reservoir of the mobile phase and positive valving for alternately connecting the pump output to a sample injection valve during a delivery stroke and to a reservoir of the mobile phase during the uptake stroke. Suitable control means, such as a microprocessor, serves to coordinate the movement of the pump plunger with the active valving.

It is preferred to provide for independent, fast return means by which the fill return stroke is driven by such means in order to refill the pump rapidly. A suitable arrangement is disclosed for connecting the pump from the fast return means for refill to the ordinary drive means during the flow stroke. The flow stroke drive means generally comprises a stepping motor coupled through a suitable gearing to the shaft of the pump plunger. Particular details of a pump structure satisfying the foregoing criteria and especially adapted for use in the present invention are disclosed and include a seal formed at the delivery end of the plunger coupled to a cylinder encasing the same. The seal can be formed by providing an outwardly facing recess formed in the delivery end of the plunger for containing a spring loaded balanced seal disposed in the recess which maintains contact with the inner wall of the cylinder during operation.

BRIEF DESCRIPTION OF THE DRAWINGS

FIG. 3 is a detailed cross sectional view of a pump design suitable for use in the present invention.

FIG. 4 is a generalized view in schematic form of a liquid chromatographic system as constructed in accordance with the present invention and adapted for gradient elution.

DETAILED DESCRIPTION OF THE PREFERRED EMBODIMENTS

Figure 1:
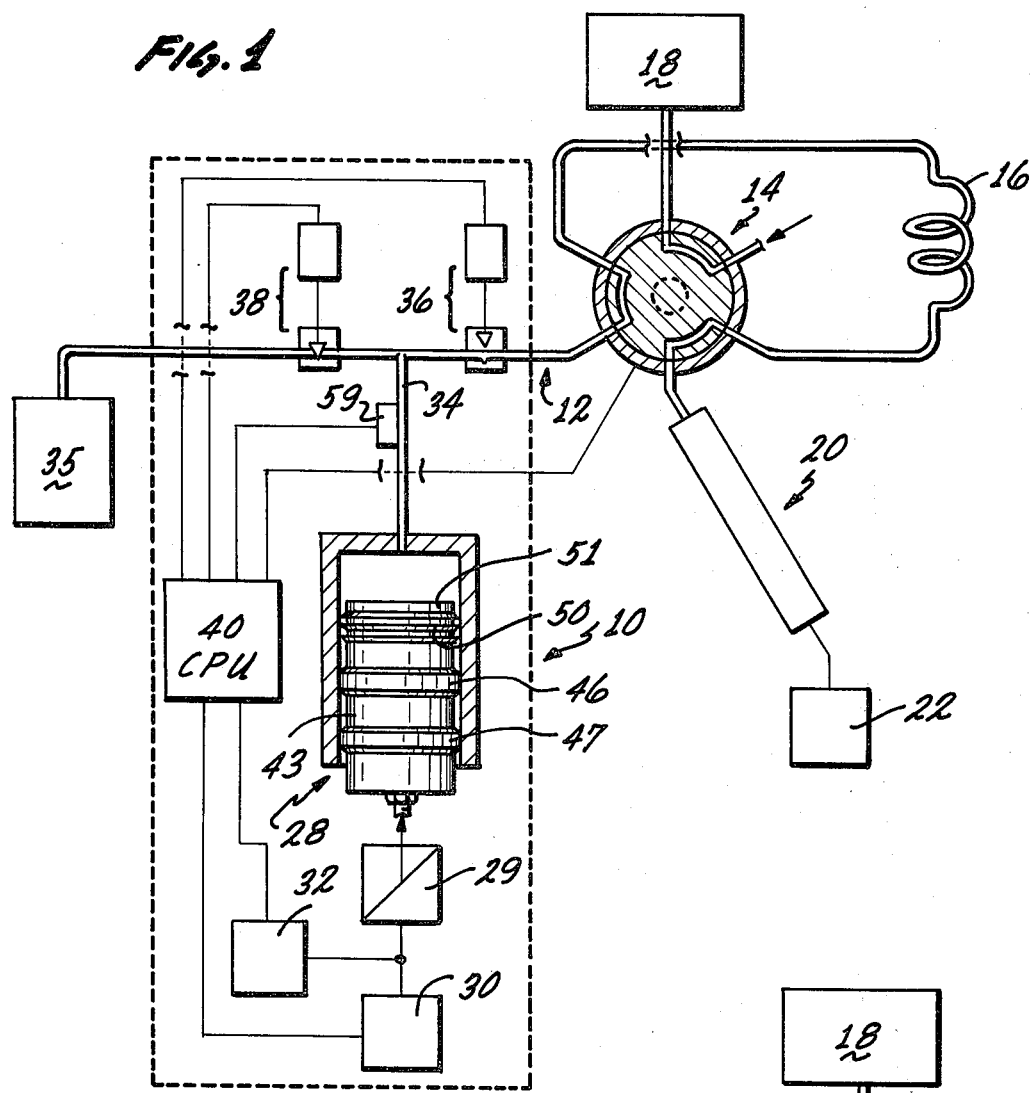
FIG. 1 is a general view in schematic form of a liquid chromatographic system module constructed in accordance with the present invention with portions shown in schematic cross-section and illustrating the same at the beginning of the sample injection stroke.
Figure 2:
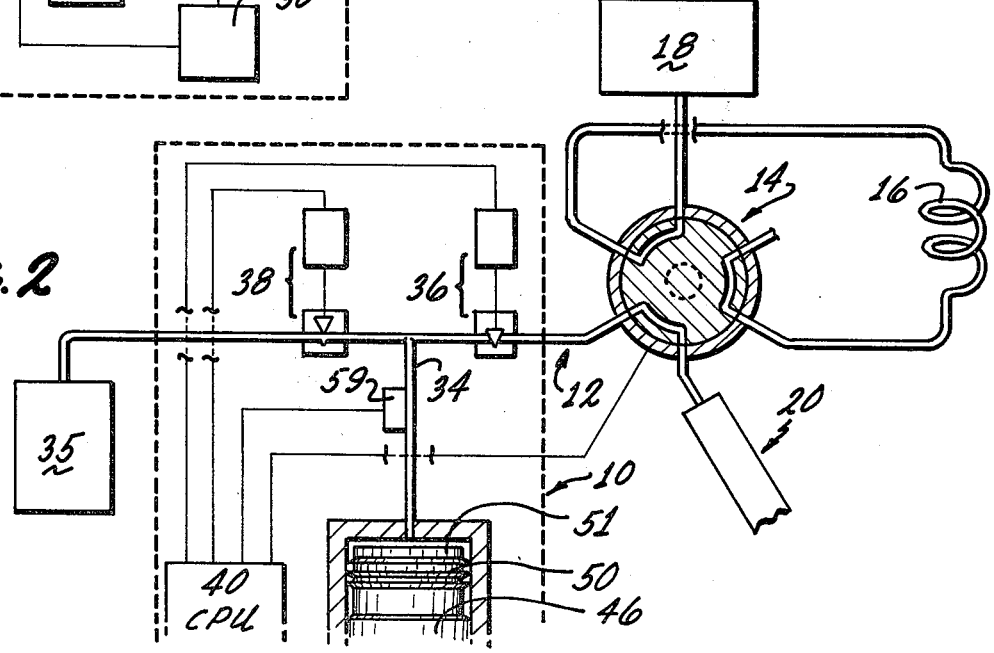
FIG. 2 is a view similar to FIG. 1 showing the module at the beginning of the refill return stroke.

Referring now in general to FIG. 1 there is shown one embodiment constructed in accordance with the present invention and suitable for isocratic liquid chromatographic elution. The general components of the system include pump module 10 having an injection output at 12 which delivers a mobile phase liquid element to a sample valve 14 having a sample retaining loop 16. The sample valve has an input connected to a sample source 18. The output of the sample valve consists of a sample carried by the mobile phase, the same being delivered to liquid chromatographic separation column 20 the output of which is passed through a detector 22.

The pump module will now be described in detail and includes a syringe pump 28 constructed in accordance with the present invention driven through suitable gearing 29 such as a ball screw by a linear stepping motor indicated at 30. The arrangement is such that the pump is driven by the foregoing means in the one direction only, namely, the pump output stroke. For reversing the pump during the refill cycle there is provided a separate motor indicated diagrammatically at 32 which operates at a much higher effective speed than the stepping motor 30. The output of the syringe pump is taken through line 34 and is connected on the one side to a sample injection valve at 14 or on the other side to a reservoir 35 of mobile phase liquid. A pair of positive acting valves 36, 38 are disposed in the output lines for connecting the pump output line 34 either to the output at 14 or to the reservoir 35 without the use of check valves (which are prone to leakage). A control module 40 or CPU is provided for controlling the motors 36, 38 in synchronism with the valving as follows: When linear stepping motor is connected to drive the piston in injection mode, inlet valve 38 is shut while outlet valve 36 is open. After completion of each run, the CPU causes motor 30 to be shut off, the valves to be reversed; that is to say inlet valve 38 is opened to the reservoir 35 while the outlet valve 36 is closed. During the refill cycle fast motor 32 overrides motor 30 and brings the piston rapidly back to refill the pump.

FIG. 3 shows a detailed construction of a pump designed for use in the present invention. There is provided an outer cylinder 41 having an inwardly facing highly polished wall surface 42 through which a plunger 43 operates in reciprocating motion. The plunger carries a pair of spaced annular guide rings 46, 47 suitably disposed in grooves 43a, 43b for stabilizing its motion. The guide rings can be of teflon and are biased into wiping contact with the wall surface by garter springs 48, 45 which provide a centering force proportional to lateral displacement of the plunger. The plunger carries at its extreme end, i.e., adjacent to its operating face, a circumferential seal 50, preferably of the balanced seal type and disposed in an outwardly facing groove formed adjacent that end of the plunger. The groove is formed by a relieved end section of the plunger at 50c and an end cap 51. The balanced seal comprises a flexible member 52, made of Teflon, and given the form of a partial toroidal shell in cross section, and having one end face open so that it is U-shaped in radial cross section and positioned with the opening facing towards the operative volume of the pump. Means are provided within the balanced seal yieldably urging the same into compliant and sealing contact between the wall of the sleeve of the pump and the groove of the contained plunger thereby providing a low pressure seal of a mechanical nature to establish the initial structural stability of the parts. Such means consists of an annular spiral spring 54 (referred to as a garter spring) inserted in the interior of the recess of the seal. The plunger is constructed with a removeable end so as to facilitate mounting of the seal. The coils of the spring are canted to the radial of the ring to provide radial deflection and to preload the same for inward and outward expansion within its physical limits of the parts. Such balance seals are well known in the art and may be obtained from the Bal Seal Engineering Company of Santa Ana, Calif.

The pump is driven by a stepping motor 30 through gearing 29, such as a ball screw device, the connection being through a suitable clutch operated in conjunction with the motor 30, i.e. when stepping motor 30 is activated, so is the clutch, the stepping motor being controlled by a CPU 58. For the refill cycle a rapid acting DC motor is interconnected to override the stepping motor for returning the pump plunger during refill.

Means is provided for sensing the pressure in the outlet line so as not to exceed design limits and consists of a pressure transducer coupled to the line as indicated at 59. The output of the syringe pump of the present invention is connected between positive acting valves 36 and 38, the valves being under the control of the CPU. The positive acting valves form a T connection one side of which goes to reservoir 35 for the refill stroke and the other side of which connects to the sample injection valve 14 and elution column 20. The valves operate alternatively, that is to say in refill mode the inlet valve 38 is open while the outlet valve 36 is closed. During injection the opposite connection is made so that the outlet is opened while the inlet side is closed. Operation of the system will now be reviewed and summarized. During the intake or refill cycle CPU activates DC motor 32 to return the plunger and withdraw the same within the syringe pump. Simultaneously the CPU activates the positive acting valves 36, 38 to open the valve 38 to the reservoir and to close the outlet valve 36. After the refill cycle is complete the CPU shuts valve 38 and opens the outlet valve 36 while simultaneously stopping the action of DC motor 32. A sample is loaded into the sample injection valve and retained in sample loop 16. The CPU activates then stepping motor 30 to drive the plunger forward. Pressure builds up to the design maximum relatively rapidly since there are very few parts having compliance in the system and the volume of the syringe pump is limited so that rapid pressure elevation is achieved without the need for compressing a large column of liquid. The sample injection valve may be activated by the operator or CPU 58 anytime after the LC System is stable. This LC system is run in the usual discharge mode until the desired length of time has passed for one sample to be analyzed, which is less than twenty minutes for most common applications.

Pump Specification (40 ml)
  Sleeve diameter—0.750 inch I.D. 1.0" O.D.
  Plunger diameter—0.745 inch
  Stroke length—6 inches
  Balanced seal dimensions—0.750 O.D. 0.562 I.D. 0.140 wide
  Positive T-valve—Model S500—(Scientific Systems, Inc.)

The following are:
Performance Specifications for a Pump Module constructed in Accordance with the present invention.
  1. Maximum total flow rate—2.0 ml/min
  2. Settable total flow rate increments—0.1 ml/min
  3. Programmable flow rate increments—0.001 ml/min
    resolution is 1:2000
  4. Programmable solvent compositional accuracy—0 to 100% ±1% or better
  5. Total volume of one pump module—40 ml
  6. Longest analysis time
    at max. flow of 3 ml/min—20 minutes
    at min. flow of 0.1 ml/min—400 minutes
  7. Maximum pressure—2000 psi or more (limited by size of stepper motor)
  8. Flow rate accuracy—±2% of set total
  9. Flow rate reproducability—±0.2% abs. at 5 min.

Referring now to FIG. 4 there is shown a generalized schematic form of a system for gradient elution utilizing two pump modules constructed in accordance with the present invention. Obviously it would be possible to use three or more to provide column gradients based on the same principles. As shown there are two sides to the pump module each of which is identical in structure. Accordingly, like parts corresponding to FIG. 1 have been given like number with the addition of the letter designation A or B. Further detailed description of the operation of the pump module components is unnecessary in view of the previous discussion. The output of the pair A and B of pump modules is taken through a mixing chamber indicated at 60 to provide a suitable mixing of the two solvents into a homogenous mobile phase. The output of the mixing chamber is then directly connected to sample injection valve 14 which operates in the manner discussed with respect to the description of FIG. 1, the output being delivered to the column for separation.

Recently instruments have been designed to use packed micro capillary columns for exceedingly high resolution of certain samples. Reference is made to the article "Techniques of Capillary Liquid Chromatography" by Yukio Hirata and Milos Novotny as set forth in Advances in Chromatography 1979 edited by A. Zlatkis and published by the University of Houston, Tex. which discusses the use of capillary separation columns. Generally speaking the cross section of such capillaries is approximately one fourth of a standard elution column. Accordingly, the present invention uses adaption thereof made to reduce the volume of the syringe pump in proportion, the volume being preferably in the order of 10 mL. The dimension of the pump and stroke length will be the same as previously described except that the diameter of the pump sleeve and plunger is reduced by a factor of two. As described in the reference, high pressure syringe pumps were used and were of the type previously referred to having excessively large volume.

While the invention set forth herein has been disclosed with reference to a specific example of one form by which it is reducible to practice, many other forms of the invention will occur to those skilled in the art to which it pertains. Thus, by way of example, while the present disclosure provides for a two motor arrangement it is possible to obtain essentially the same functional result by changing the stepping drive pattern (repetition rate) to vary to a much higher rate only during the refill cycle.

What is claimed is:

1. In LC apparatus, a separation column having a stationary phase through which a pump drives a mobile phase containing a sample having components to be separated by differential adsorption as the sample is passed through the stationary phase, a sample injection valve, a one shot delivery system comprising a pump, means for refilling the pump including a reservoir of said mobile phase, a first positive actuated valve for connecting the pump output to said sample injection valve during a delivery stroke, a second positive activated valve for connecting said pump to said reservoir of said mobile phase during the uptake stroke, means for driving the pump to deliver therefrom precise quantities of the said mobile phase to the sample injection valve, fast return motor means, means for connecting the pump to said fast return means during the uptake stroke, means for synchronizing and controlling the foregoing elements such that said first valve is opened and said second valve is closed during the uptake stroke as operated by said fast return motor means while said first valve is closed and said second valve is opened when the pump is connected to said first motor means for said delivery stroke.

2. In LC apparatus as in claim 1 in which said pump has a delivery stroke capacity of about 10–40 ml.

3. LC apparatus as in claim 1 in which said pump comprises a plunger and a sleeve housing having an inner wall, means forming a slidable linear motion seal between said plunger and said sleeve housing including means forming an outwardly facing annular recess in said plunger at the delivery and thereof, a spring loaded, balanced seal disposed in said recess, the inner wall of said sleeve being smooth throughout the path of travel of said seal during the delivery stroke.

4. A gradient elution system for LC as in claim 1 wherein said column comprises an elongate capillary tube and in which the volume of each of said syringe pumps is about 40 ml.

5. LC apparatus as in claim 1 in which said pump comprises a cylinder, forming a sleeve wall, a plunger, means forming a balanced seal disposed and carried on the plunger at its delivery end, guide and seal means disposed at spaced locations on the plunger for yieldably centering the same and for providing a secondary seal against leakage.

6. LC apparatus as in claim 5 in which said balanced seal comprises a flexible member of toroidal cross section having one side open toward the delivery end of said plunger.

7. An LC apparatus as in claim 6 further including a garter spring disposed in said flexible member for yieldably urging the same into contact with said sleeve wall.

8. In a gradient elution system for use in liquid chromatography, at least first and second eluent pump modules, means for controlling said modules to combine their outputs to correspond to predetermined percentages, a mixing chamber for receiving the combined output of said modules, a sample injection valve connected to the output of the mixing chamber, a separation column having an inlet connected to the output of said sample injection valve for separating the components of said sample as carried there through by said mobile phase of each of said modules, each of said pump modules comprising a one shot delivery system comprising a pump, means for refilling the pump including a reservoir of said mobile phase, a first positive actuated valve for connecting the pump output to said sample injection valve during a delivery stroke, a second positive actuated valve for connecting said pump to said reservoir of said mobile phase during the uptake stroke, means for driving the pump to deliver therefrom precise quantities of the said mobile phase to the sample injection valve, fast return motor means, means for connecting the pump to said fast return means during the uptake stroke, means for synchronizing and controlling the foregoing elements such that said first valve is opened and said second valve is closed during the uptake stroke as operated by said fast return motor means while said first valve is closed and said second valve is opened when the pump is connected to said first motor means for said delivery stroke.

* * * * *